US008792095B2

(12) United States Patent
Piorek et al.

(10) Patent No.: US 8,792,095 B2
(45) Date of Patent: Jul. 29, 2014

(54) METHODS AND APPARATUS FOR TRANSPORT OF AIRBORNE MOLECULES USING AN ACTIVE CYCLICAL VAPOR/LIQUID EXCHANGE

(75) Inventors: Brian D. Piorek, Santa Barbara, CA (US); Carl D. Meinhart, Santa Barbara, CA (US); Seung Joon Lee, Santa Barbara, CA (US)

(73) Assignee: OndaVia, Inc., Hayward, CA (US)

( * ) Notice: Subject to any disclaimer, the term of this patent is extended or adjusted under 35 U.S.C. 154(b) by 307 days.

(21) Appl. No.: 13/318,983

(22) PCT Filed: May 7, 2010

(86) PCT No.: PCT/US2010/034127
§ 371 (c)(1),
(2), (4) Date: Feb. 6, 2012

(87) PCT Pub. No.: WO2011/016888
PCT Pub. Date: Feb. 10, 2011

(65) Prior Publication Data
US 2012/0127465 A1    May 24, 2012

Related U.S. Application Data

(60) Provisional application No. 61/176,473, filed on May 7, 2009.

(51) Int. Cl.
*G01J 3/44* (2006.01)
*G01N 33/00* (2006.01)
(52) U.S. Cl.
CPC ................. *G01N 33/0057* (2013.01); *C02F 2209/00* (2013.01)
USPC ....................................... 356/301

(58) Field of Classification Search
USPC .............................. 356/72–73, 301
See application file for complete search history.

(56) References Cited

U.S. PATENT DOCUMENTS

2004/0063214 A1*   4/2004   Berlin et al. ............ 436/94
2006/0275541 A1   12/2006   Weimer
(Continued)

FOREIGN PATENT DOCUMENTS

WO    WO 2009/020479 A2    2/2009

OTHER PUBLICATIONS

Piorek, B. et al.; "Free-surface microfluidic control of surface-enhanced Raman spectroscopy for the optimized detection of airborne molecules," Proceedings of the National Academy of Sciences of the United States of America [online] 2007, 104(48), 18898-18901 [Retrieved on Dec. 26, 2010 and May 25, 2012] Retrieved from the Internet URL:http://www.pnas.org/.

(Continued)

*Primary Examiner* — Abdullahi Nur
(74) *Attorney, Agent, or Firm* — NUPAT, LLC

(57) ABSTRACT

Methods and apparatus for detection and/or analysis of gas phase analytes and chemical compounds. The apparatus can be formed with microfluidic cells containing a selected fluid that interacts with the analyte(s), wherein the fluid can selectively transition between a vapor phase and a liquid phase. During condensation of the fluid, the population of analytes present within the vapor phase region of the fluid can be transported into the liquid phase region of the fluid within the microfluidic cells. During evaporation of the fluid, the analytes can be substantially retained within liquid phase region of the fluid and within the cells. Repetitive cycling of this vapor/liquid exchange can provide a build-up of the analytes within the microfluidic cells where they can be detected/analyzed.

10 Claims, 13 Drawing Sheets

(56) References Cited

U.S. PATENT DOCUMENTS

2007/0048746 A1  3/2007  Su et al.
2007/0165217 A1  7/2007  Johansson et al.
2009/0213369 A1  8/2009  Lee et al.

OTHER PUBLICATIONS

PCT/US2010/034127 International Search Report dated Jan. 11, 2011.

* cited by examiner

METHODS AND APPARATUS FOR TRANSPORT OF AIRBORNE MOLECULES USING AN ACTIVE CYCLICAL VAPOR/LIQUID EXCHANGE

CROSS-REFERENCE

This application is filed pursuant to 35 U.S.C. §371 as a United States National Phase Application of International Application Ser. No. PCT/US10/034,127, filed May 7, 2010, which claims the benefit of U.S. Provisional Application No. 61/176,473, filed May 7, 2009, both of which are incorporated by reference herein in their entirety.

STATEMENT AS TO FEDERALLY SPONSORED RESEARCH

This invention was made with the support of the United States government under Contract number W911NF-09-D-0001 and W911NF-08-R-0006 by US Army RDECOM ACQ CTR.

FIELD OF INVENTION

The invention relates to capturing airborne chemical species in the gas phase. More particularly, the invention relates to detection and/or analysis of low concentration chemical species using a fluid medium that transitions between vapor and liquid phases.

BACKGROUND

Low concentrations of chemical species (analytes) targeted for detection and analysis pose unique technical challenges. Because low-concentration detection and analysis of some chemical compounds necessitate large and heavy lab apparatus, field deployment is often rendered difficult or impossible. In addition, the targeted analytes may be contaminated and/or mixed with false-positive compounds that confound accurate detection and analysis.

By definition, low concentrations generally represent a high ratio of inert or untargeted compounds to the targeted compound(s), often necessitating a process of filtering or other concentration processes, and with or without isolation or removal of contaminants. Thus, preparation is required to isolate and concentrate the analytes prior to the detection/analytic process, also inhibiting field portability.

There is a need for apparatus and processes that are both field portable and accurate, yielding minimal false-positive and false-negative detection events, and offering accurate and repeatable detection/analysis of the targeted analyte(s). Applications include hand-held chemical detectors for low-concentration analytes such as drugs, explosives, chemical and/or biological agents and weapons used in terrorist activities, and biological metabolites.

SUMMARY OF INVENTION

The invention provides systems and methods for analyzing and/or detecting airborne analytes. Various aspects of the invention described herein may be applied to any of the particular applications set forth below or for any other types of microfluidic or nanofluidic devices. The invention may be applied as a stand alone system or method, or as part of an integrated solution, such as a portable analyte detection system. It shall be understood that different aspects of the invention can be appreciated individually, collectively, or in combination with each other.

An aspect of the invention provides microfluidic devices for various applications. In a preferable embodiment of the invention, a device may be formed with a plurality of microfluidic cells and/or microcells. In some instances, the cells and/or microcells are volumes formed with a substrate (e.g., silicone, polymer, or glass) of the microfluidic device. One or more of the cells may in turn consist of one or more active regions therein.

The cells may be preferably formed with a diameter ranging from approximately 10 nanometers to 1000 micrometers, or from about 10 nanometers to about 200 nanometers. In specific embodiments, the cell has a diameter of about 1 micron to about 100 microns, e.g., with a nominal diameter of 5 microns, or about 20 microns. In other preferable embodiments, the cell can be formed with a diameter of 0.5 microns to 500 microns, more preferably with a nominal diameter of 5 microns. Furthermore, the cells may be preferably formed with a depth ranging from approximately 10 nanometers to about 1000 microns, or about 100 nanometers to about 1000 nanometers. In preferable embodiments, the cells can be formed with a nominal depth of about 500 nanometers.

A selected liquid such as water may be contained or confined over nanostructured surfaces within the microfluidic cells, which interact with a targeted analyte, either chemically or physically. The liquid may be selected for its relative affinity or repulsiveness to a particular analyte or class of analytes, thus substantially excluding contaminants and/or non-selected chemical species, thereby facilitating desired concentration and specificity for the analyte. In certain embodiments, one or more cells of a device provided herein has a flood-evaporation depth of liquid-phase fluid of about 1 nanometer to about 1000 microns, e.g., with a nominal flood-evaporation cycle level of about 10 nm to about 100 microns.

In some embodiments of the invention, the microfluidic device comprises an air/liquid interface providing selectivity for a targeted molecule. In some instances, selectivity occurs by allowing polar molecules to partition into the aqueous liquid and non-polar molecules to not partition into the liquid. In certain instances, this is a result of the relative values of Henry's constants between various analyte molecules. The condensed liquid medium provides concentration of the analyte molecules, which may be quantified by the absolute value of the associated Henry's constant. The level of concentration can be significant under equilibrium conditions, but it may take a significant amount of time to reach equilibrium. Thus, in some embodiments, a microfluidic device provided herein comprises a mechanism (e.g., one or more components or device) for active cycling of the liquid/vapor exchange.

In certain embodiments, active cycling of the liquid/vapor exchange includes actively evaporating the liquid (i.e., the condensed form of the fluid used in a device described herein, such as, e.g., water) and/or actively condensing the vapor (i.e., the evaporated form of the fluid used in a device described herein, such as, e.g., water). Active cycling of the liquid/vapor exchange can be achieved utilizing any suitable component, device or process. In specific embodiments, active cycling is achieved, e.g., through any active pumping process, including, by way of non-limiting example, heating and/or cooling processes or cycling, reduced and/or elevated pressure processes or cycling, or the like. In certain embodiments, evaporating the fluid (e.g., a solvent of the analyte) and condensing the fluid (e.g., a solvent of the analyte) are performed concurrently, sequentially, alternately, or the like. In some instances, the time constraint to reach equilibrium conditions can be reduced substantially by active pumping of the liquid/vapor exchange at the free surface. This "active pumping" can be achieved in any suitable manner, including, e.g., temporally cycling the local temperature of the liquid region above and below the ambient dew point. Generally, and in preferred embodiments, analyte molecules (e.g., targeted or selected molecules) that are captured in the liquid do not evaporate at the same rate as the liquid evaporates. Thus, in certain embodiments, the analyte molecules (e.g., targeted or selected molecules) remain in one or more of the cells and are available for detection (e.g., in some instances, the molecules adsorb to a surface-enhanced Raman scattering (SERS) active surface such as one or an assembly of nanoparticles or nanowires/nanorods, or any other suitably nanostructured metal surfaces, or an assembly of nanoparticles onto metal or non-metal substrate surfaces) within a microfluidic device described herein).

In some embodiments, the duty cycle rate of active pumping of the liquid/vapor exchange is effectively substantially zero. In other words, in certain embodiments, at a given time, a substantially similar amount of liquid is evaporating as is condensing within a device or cell provided herein (i.e., the volume of the liquid in the device, or a cell thereof, is essentially static).

Certain embodiments of the invention include microfluidic devices with integrated electrical leads positioned about one or more active region(s). The electrical leads can be alternatively switched to function as: (i) resistive elements to facilitate evaporation; and/or (ii) capacitive leads to facilitate sensing of a liquid level. As analytes interact with formed nanostructures within a liquid-phase fluid, they can be detected and/or analyzed using a variety of technologies. For example, the analytes may undergo or be studied using methods such as surface enhanced vibrational spectroscopy, surface plasmon resonance spectroscopy, electrochemical analysis techniques which may include molecular recognition elements, fluorescent chemical marker techniques, fluorescence quenching, redox-labeled nucleic acid binding techniques (including, but not limited to, the molecules DNA, RNA and PNA), X-Ray absorption techniques, IR, visible, UV, and other electromagnetic radiation absorption and spectroscopic techniques, mass spectroscopy techniques, liquid chromatography techniques, flame ionization analysis techniques, DNA melting point techniques, or titration analysis techniques.

In another embodiment, laser radiation may be preferably applied to the microfluidic cell(s) to evaporate a condensed, analyte-bearing, liquid-phase fluid. Other heat or radiation sources may be selected to evaporate a selected fluid. In various embodiments, evaporation of a liquid provided herein is achieved in any suitable manner including, by way of non-limiting example, by heat-driven evaporation (e.g., by incorporation of heating elements into a microfluidic device, or one or more cells thereof, described herein to effect controlled evaporation of medium); laser-induced heating (e.g., by use of separate heating laser; by incorporation of LCDs to selectively increase absorption of laser radiation; by selective heating (along fluid channel) via scanning and dwell controls; by incorporation with SERS interrogation laser; by incorporation of ultrasonic transducers to effect evaporation/atomization; or the like); by vacuum-driven evaporation (e.g., including application of vacuum cycling to effect evaporation of fluid; vacuum cycling in presence of zeolite to enhance evaporation and reduce temperature; or the like); by RF-driven evaporation (e.g., including exposure to microwave radiation to effect evaporation of fluid; incorporation of magnetron(s) and waveguide(s) with fluid channel(s); or the like); by electrolysis-driven evaporation (e.g., including incorporation of pos/neg (+/−) electrodes into channel to reduce fluid; incorporation of Pd/Pb contacts to effect catalysis; using free hydrogen and oxygen ions may be used to augment SERS spectra; or the like); convective evaporation by application of controlled gas stream; or the like.

In some embodiments, provided herein is an active pump described herein contains active condensation sites, e.g., which have sharp walls and corners, that facilitate condensation. In certain embodiments, one or more of the cells described herein comprises a condensation site. In specific embodiments, the condensation site is at a sharp angle between a first surface, such as a wall (e.g., the wall of a cell, pillar, or the like), and another surface, e.g., the bottom of the cell or the surface of the liquid in the cell. Such sharp angles and walls can be seen in the illustrations of, e.g., FIGS. 1, 3, 6, 7, 8, and 10. Moreover, in certain embodiments, a typical sensing region, e.g., for detecting an analyte with any detection device described herein, will be in or near a condensation site of a cell.

In certain embodiments of the invention, a microfluidic array is provided that can be divided into single or multiple regions. One or more different measurements and analysis/detection techniques may be performed within the same array. For example, a selected region of the array can be used for SERS-only measurements, and another region of the array can be used for ordinary, non SERS, Raman-only measurements. Other adjacent regions may be divided and specified for yet other analytical measurements. Alternatively, SERS and ordinary Raman measurements may be performed together in one common region. For certain applications, the concentration of an analyte (via cyclical flooding and evaporation of an analyte-bearing, liquid-phase medium, in accordance with other aspects of the invention) can facilitate SERS interrogation up to a certain extent. However, extended concentration can produce a crystalline solid in order to prepare a ordinary Raman (not SERS) interrogation. It shall be noted that when using ordinary Raman measurement, quantitative analysis is usually more facile than SERS due to a more linear response of ordinary Raman vs. SERS and availability of a Raman library.

As discussed above, in some embodiments, analyte molecules adsorb to a SERS-active surface within a microfluidic device described herein as a result of active pumping of the liquid/vapor exchange. In certain embodiments, this adsorption of the molecule to the SERS-active substrate is used to amplify a Raman signal from the analyte molecules by many orders of magnitude. In some embodiments, the Raman signal is excited and collected by a confocal Raman probe. The resulting Raman spectrum can be analyzed using any suitable technique (e.g., chemometric numerical analysis techniques) to obtain specificity of the detected molecule.

In preferable embodiments provided herein, devices and processes may utilize several physical processes to obtain highly sensitive and specific measurements of airborne chemicals (see FIG. 1). In some instances, airborne molecules (e.g., airborne molecules targeted or selected for detection) are transported to the absorption region by advecting ambient air.

Another embodiment of the invention provides a microfluidic device formed with active regions featuring a series of raised or embossed structures (e.g., pillars or spikes). These structures may be also modified or contain smaller-scale features to support or enhance nucleation of an analyte-bearing fluid, thus increasing the transport of selected analytes into the selected medium. In another preferable embodiment, the active regions may be formed with or utilize sharp wall angles to enhance nucleation during condensation of the analyte-bearing, gas-phase fluid.

In a preferable embodiment, the aforementioned active regions can be deployed in a series of integrated arrays. The arrays can be interlinked by electrical leads to facilitate resistive heating, level sensing within the medium, and/or selective multiplexing of said active regions. Such arrays may also deploy multiple uniform active regions to enhance the accuracy of single-species analyte detection/analysis by redundancy, or multiple, non-uniform detection arrays capable of detecting/analyzing a multiplicity of analytes.

A variety of closed-feedback controls can be selected for use with the apparatus and methods described herein. One or more controls can be established to perform various functions and manage the exchange between flooding and heat- or pressure-driven evaporation controls, level sensing of media, detection/analysis, and/or multiplexing of microchannels, cells, and arrays. In addition, feedback controls may be monitored to facilitate off-line signal analysis and detection.

Other aspects of the invention provide methods of capturing and transporting gas phase particles utilizing microfluidic devices for detection, analysis and/or other applications. In preferable embodiments of the invention, methods are provided for concentrating relatively low concentration analytes or particles. Such analytes may be transported from a gas-phase fluid to a liquid-phase fluid during a condensation step. The analytes may be concentrated through an alternately repeated or cyclical process of flooding and heat- or pressure-driven evaporation of the fluid, thus separating the evaporating liquid-phase fluid from a formation of increasingly concentrated analytes which remain in the proximity of nanostructured surfaces formed within the devices. In a preferable embodiment, an overlayer of inert material (e.g., $SiO_2$) may be deposited upon a nanostructured surface to allow physical interaction with targeted analytes thereon, but inhibit chemical bonding, such that reuse and cleaning of the active sites is facilitated.

Some embodiments of the invention provide methods of concentrating analytes in apparatus for selected detection or analysis. The apparatus may include devices formed with microfluidic cells that facilitate cyclical condensation of a desired fluid such as water. Since many molecules (for instance DNT and TNT) exhibit a relatively low vapor pressure, these species may partition rapidly from a vapor phase into a liquid phase as water vapor condenses into the microfluidic cells (as described by Henry's Law). By first transferring into a condensing vapor during a condensation process, these low vapor pressure species can be driven to transfer into the microfluidic cells by the forced condensation of water vapor above the microfluidic cells. These processes can thereby allow production of a 3-dimensional sampling volume comprised of the water vapor existing above the microfluidic cells from which airborne analyte species are transferred into the microfluidic cells for analysis or detection. Once the condensed water vapor containing analyte is formed in the microfluidic cell after condensation commences, the affinity of analyte molecules to the walls of the microfluidic cells, nanostructured substrate, or inert material added above the nanostructured substrate can cause or encourage the analyte to remain in the microfluidic cell over multiple heating/cooling cycles. Upon heating after condensation, the liquid phase is driven from the microfluidic cells, causing a concentration effect of analyte which remains adhered to microfluidic cell walls, nanostructured substrate, or inert material added above the nanostructured substrate.

Within embodiments providing colloidal nanoparticles for SERS enhancement for analyte detection, nanoparticle aggregation may be controlled by the injection of non-analyte molecules or compounds. These molecules or compounds preferably do not produce SERS spectra which substantially interfere with the detection of analytes of interest. For instance, sodium chloride may be added by controlled means to the nanoparticle solution to cause aggregation by charge collapse. In another embodiment, a 'nanoparticle linker molecule' such as 1,2-diaminoethane, 1,4-diaminobutane or 1,3,5-triaminopentane may be added in gaseous form to the gas-phase analyte or injected into the nanoparticle solution to cause nanoparticle aggregation and SERS enhancement of analyte molecules.

In some embodiments, provided herein is a microfluidic system for the detection of gas phase and/or airborne analytes in a condensed liquid, the system comprising:
  a. at least one condensation site comprising a microcell with a bottom surface, enclosed sidewalls, and at least a partially open top surface, wherein at least one microcell contains nanostructures;
  b. a cyclical vapor/liquid exchange pumping system; and
  c. a Raman spectrometer.

In certain embodiments, provided herein is a process of detecting or measuring the presence or amount of a gas phase and/or airborne analyte molecule in an air sample, the process comprising:
  a. condensing a vapor in at least one microcell containing a nanostructured material;
  b. confining the liquid in the microcell
  c. contacting the sample of air with the surface of the liquid;
  d. cycling the liquid through evaporation and condensation phases, whereby analyte molecules condense with the liquid into one or more of the cells, and whereby analyte molecules aggregate with and/or deposit on the nanostructured material;
  e. interrogating the microcell with a Raman spectrometer; and
  f. determining the presence of or amount of analyte molecules present in the air sample based on the Raman spectrum.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The foregoing features and other aspects of the invention are explained in the following description taken in conjunction with the accompanying figures. Further understanding of the features and advantages of the invention will be obtained by reference to the following detailed description that sets forth illustrative embodiments, in which the principles of the invention are utilized.

DETAILED DESCRIPTION OF INVENTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Figure 1:
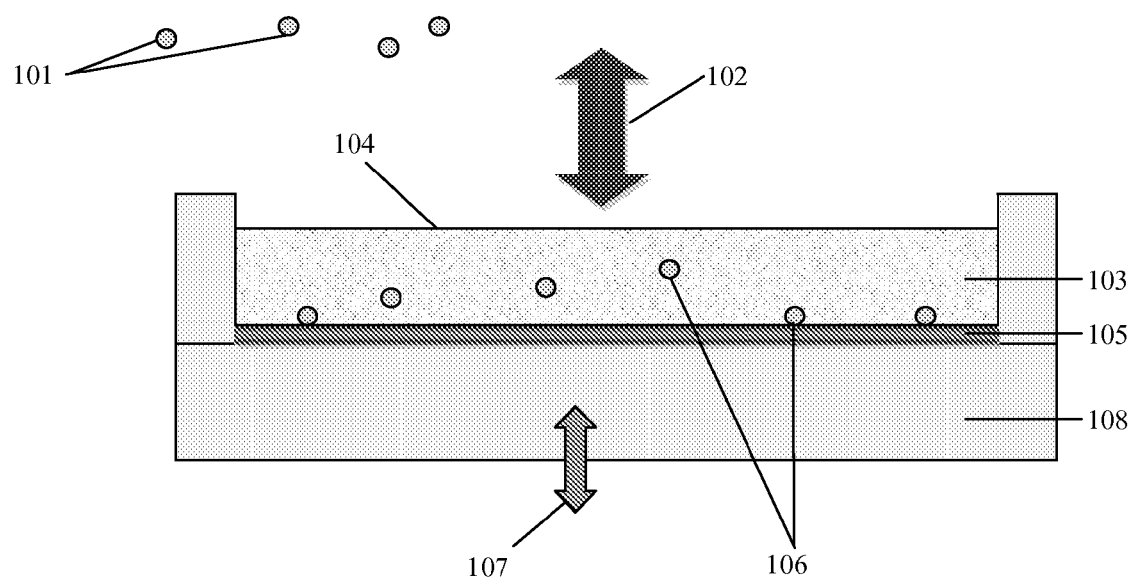
FIG. 1 illustrates a process and device useful for creating high selectivity, concentration of an analyte and amplification of signal of an analyte according to certain embodiments of the present invention.

Referring to FIG. 1, airborne molecules (101) can be transported to the absorption region in any manner, e.g., by advecting ambient air. In some instances, the air/liquid (e.g., air+vapor/liquid) interface provides selectivity (104) by allowing polar molecules to partition into the aqueous liquid and non-polar molecules to not partition into the liquid. This is a result of the relative values of Henry's constants between various analyte molecules. The condensed (liquid) medium (103) provides concentration of the analyte molecules (106), which is quantified by the absolute value of Henry's constant. The level of concentration can be significant under equilibrium conditions, but it may take a significant amount of time to reach equilibrium. The time constraint to reach equilibrium conditions can be reduced substantially by active pumping of the liquid/vapor exchange (102) at the free surface. This so-called active pumping can be achieved temporally cycling the local temperature of the liquid region above and below the ambient dewpoint. Further, in some embodiments, active heat exchange is provided by methods, devices and systems described herein (107). Analyte molecules that are captured in the liquid cannot evaporate at the same rate as the liquid evaporates. As a result, they adsorb to a SERS-active surface or region (105). The SERS-active substrate can then be used to amplify a Raman signal from the analyte molecules by many orders of magnitude. Moreover, such devices and systems may comprise any suitable substrate (108).

Figure 2:
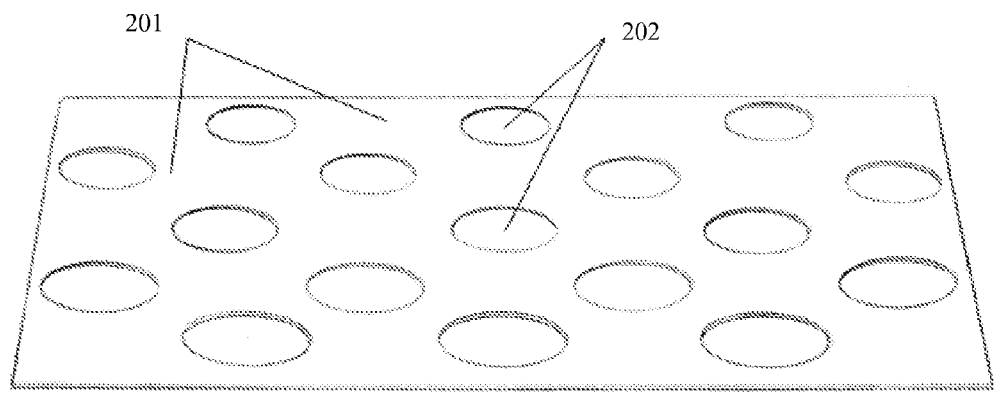
FIG. 2 illustrates one embodiment of the invention with an array of active microfluidic cell sites, wherein said sites are etched or formed into a substrate material.

Referring to FIG. 2, a plurality of microfluidic cells (202) can be etched or otherwise formed into a substrate (201) for a variety of applications in accordance with the invention. Typically, the substrates can be formed of silicon, polymers or glass. The cells may be arrayed individually or as a plurality. The geometry of cells may be selected for various purposes such as to enhance nucleation of an analyte-bearing condensate, and to facilitate ease of manufacture. The cells may be configured in round, square, rectangular, or other, more complex geometries. It shall be understood that all aspects of the invention described herein can be applied to devices interchangeably formed with cells, microcells, wells and/or microwells. In certain instances, microfluidic cells may comprise blind holes, or recesses (202), and preferably do not go all the way through the substrate.

In some embodiments of the invention, typical dimensions of cells may range from approximately 10 nm-1000 microns in diameter (width), or about 1 micron to about 100 microns, with, e.g., a nominal diameter of about 5 microns, or about 20 microns, and furthermore with a depth of about 10 nm-1000 microns, or about 100-1000 microns, with a nominal depth of about 500 nm.

Figure 3:
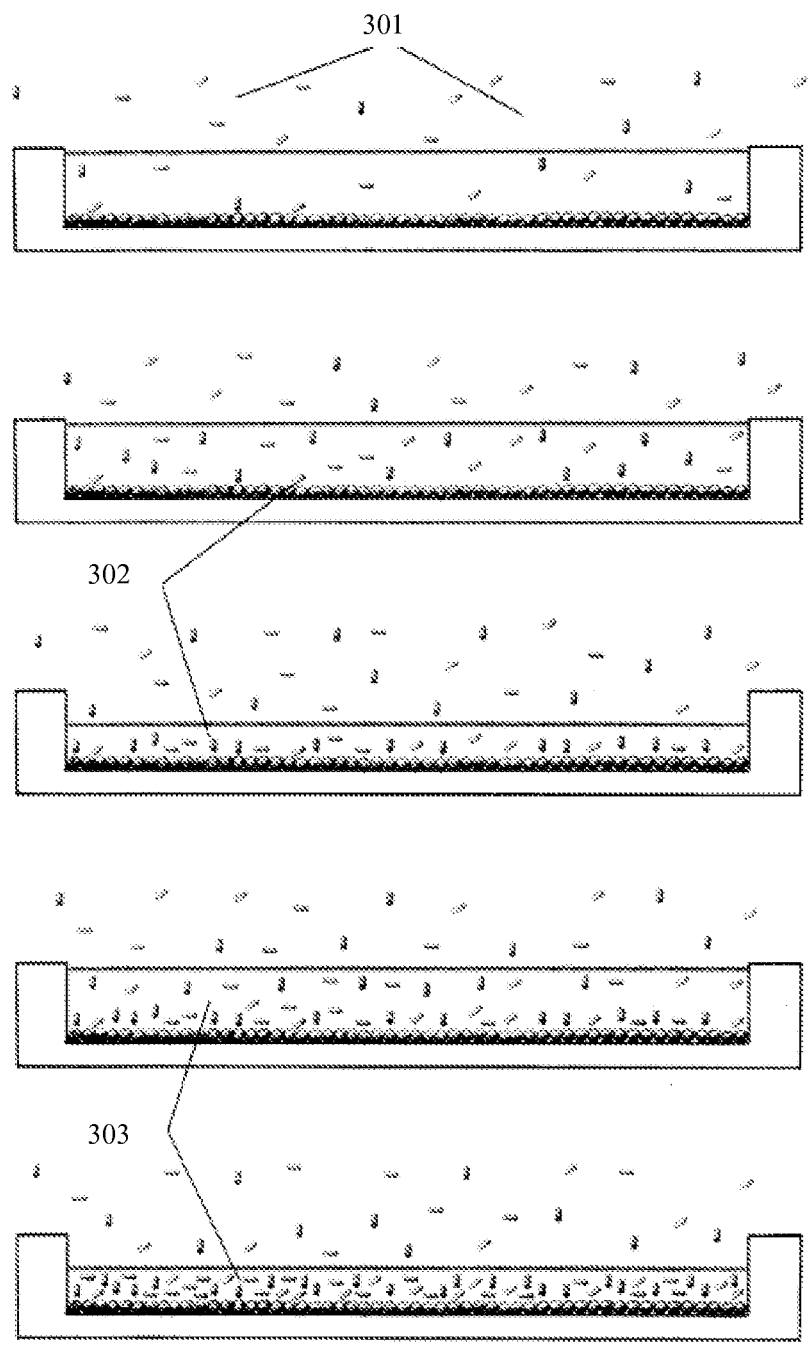
FIG. 3 illustrates one embodiment of the invention wherein condensative-evaporative concentration of analytes is facilitated within active microfluidic cell sites on nanostructured substrate via cyclical flooding and evaporation.

FIG. 3 illustrates a microfluidic cell among one or many formed in a device in accordance with the invention (presented in cross-section). A fluid may be selected for operation with the device that includes two phases: a liquid phase and a gas phase. The microfluidic cell(s) may contain therein a fluid in the liquid phase that has a particular affinity for one or more targeted analyte(s). At the same time, the fluid in the gas phase (301) may contain the targeted analyte. The liquid-phase fluid's chemical affinity for the analyte(s) may be considered and designed to enhance transport of analytes from the gas-phase fluid to the liquid-phase fluid, and to substantially exclude or isolate contaminants, spoofing compounds, and chemical "noise." Moreover, FIG. 3 illustrates sharp wall angles. In some instances, the surfaces may be roughened, e.g., by the inclusion of nanostructured substrates, which can be used to enhance nucleation during condensation of the analyte-bearing, gas-phase fluid.

The microfluidic cells within the device can be subjected to a series of cyclical flooding and evaporation cycles. One or more cells may be filled with a desired fluid at selected intervals. A number of fluid heat- or pressure-driven evaporation cycles (302) may be also performed, thus volumetrically concentrating the targeted analytes within the liquid-phase fluid. The microfluidic cells can be formed with nanostructured (bottom or side) surfaces. The analytes within the liquid-phase fluid can interact with nanostructured bottom surface of the microfluidic cells (303), where they are detected/analyzed via such methods as surface enhanced vibrational spectroscopy, surface plasmon resonance spectroscopy, electrochemical analysis techniques which may include molecular recognition elements, fluorescent chemical marker techniques, fluorescence quenching, redox-labeled nucleic acid binding techniques (including, but not limited to, the molecules DNA, RNA and PNA), X-Ray absorption techniques, IR, visible, UV, and other electromagnetic radiation absorption techniques, mass spectroscopy techniques, liquid chromatography techniques, flame ionization analysis techniques, DNA melting point techniques, or titration analysis techniques.

In other embodiments, the microfluidic cells are exposed to a gas-phase fluid containing the analyte(s). The analytes can be transported into the liquid-phase medium, and chemically or physically interacting with nanostructures (via adsorption of analytes onto surfaces by chemisorption and/or physisorption), where they are detected/analyzed via such methods as surface enhanced vibrational spectroscopy, surface plasmon resonance spectroscopy, electrochemical analysis techniques which may include molecular recognition elements, fluorescent chemical marker techniques, fluorescence quenching, redox-labeled nucleic acid binding techniques (including, but not limited to, the molecules DNA, RNA and PNA), X-Ray absorption techniques, IR, visible, UV, and other electromagnetic radiation absorption and spectroscopic techniques, mass spectroscopy techniques, liquid chromatography techniques, flame ionization analysis techniques, DNA melting point techniques, or titration analysis techniques. The detection and analysis of the gas-phase analyte can be enhanced by selecting a liquid-phase medium optimally matching the polarity of the targeted analyte(s) for maximal solubility, then concentrating said analyte(s) in the medium through cyclical condensation and evaporation within the microfluidic cells to enhance the transport of analyte existing in the gas phase into the liquid. The nanostructure(s) may be coated with a thin layer of inert material (e.g., $SiO_2$) or other chemical species to protect them from permanently binding with analytes and/or contaminants, and to facilitate cleaning and repeated use. Special structures and geometries may also be incorporated into the cells to enhance condensation and nucleation of the liquid-phase fluid.

In some preferable embodiments of the invention, typical flood-evaporation depths of a liquid-phase fluid can range from approximately 1 nm to 1000 μm, with a nominal flood-evaporation cycle level of about 10 nm to 100 μm.

Furthermore, the flow rate of the analyte-bearing fluid in the gas phase may be controlled or regulated. The flow rate can be changed to optimize or regulate the exposure and the transport of analytes from the gas-phase fluid to the liquid-phase fluid. In preferable embodiments of the invention, typical flow rates of the gas-phase fluid range near 10 cc/sec for a microfluidic cell having a nominal width of about 5 microns, or about 20 microns. It shall be understood that flow rates can be selected depending on other factors including the overall dimensions and configuration of particular microfluidic cells.

Figure 4:
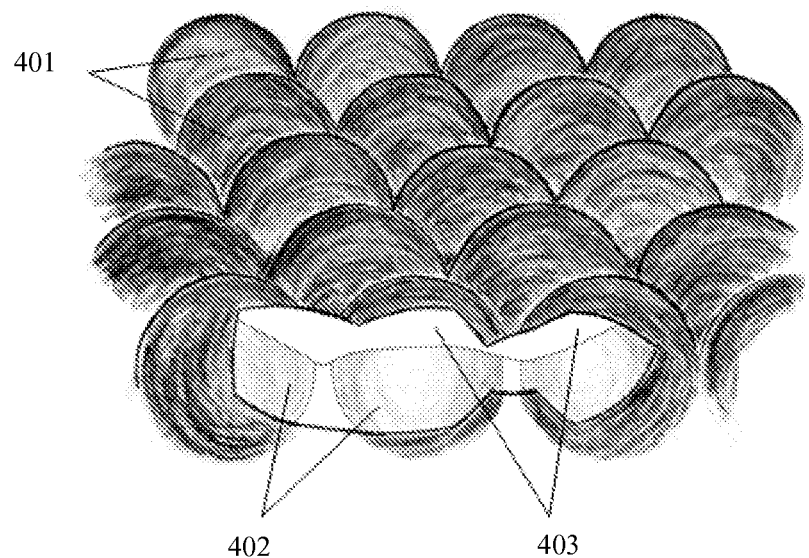
FIG. 4 illustrates one embodiment of the invention with a deposited active region of nanostructures having a deposited inert overlayer (e.g., $SiO_2$).

Referring to FIG. 4, the surface of the microfluidic cells described herein can be nanostructured (401) to improve or affect interaction with targeted analytes. For example, the cell surfaces can be modified with nanostructures to enhance chemical interaction with the analytes. A variety of nanostructuring techniques may be chosen to provide modified cells surfaces such as etched surfaces, electrochemical roughening, deposited or adhered nanospheres (402), fibers, tubules, etc. to enhance or achieve desired chemical interaction with the targeted analytes. Moreover, the nanostructured surface may be overlain with a thin layer of inert material (403) such as $SiO_2$ to inhibit permanent binding of the targeted analytes and to facilitate cleaning and reuse. It shall be understood that other nanostructures and covering materials used in microfluidic devices can be selected for use with the invention.

In some preferable embodiments, nanostructure materials may typically consist of gold (Au) or silver (Ag). In some embodiments, the cells surfaces are formed with diameters of nanospheres preferably ranging from approximately 15-100 nm for Ag and Au.

Figure 5:
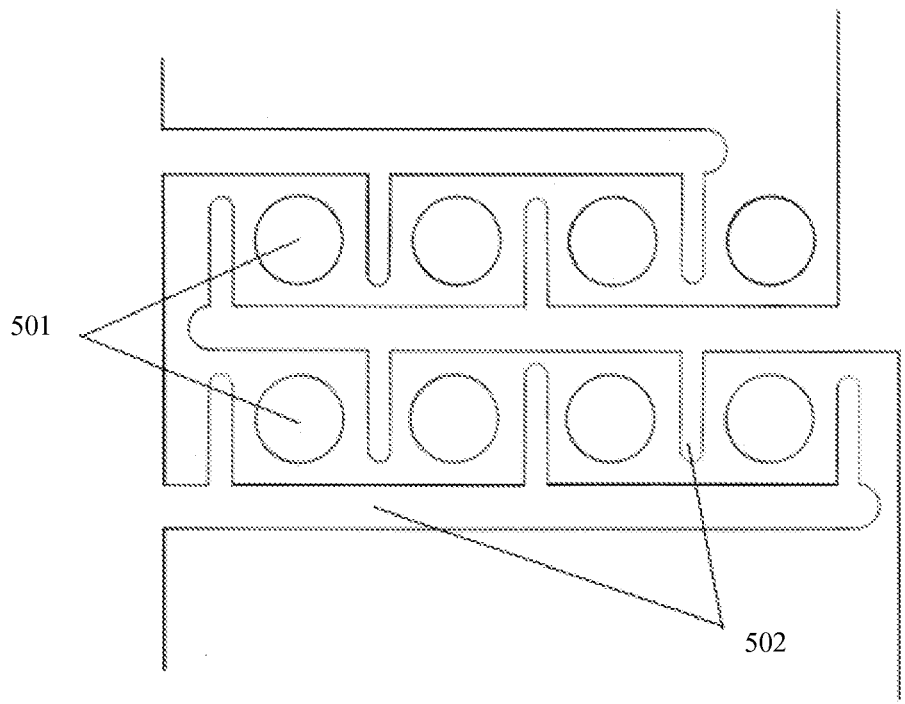
FIG. 5 illustrates one embodiment of the invention wherein active microfluidic cell sites are abutted by electrical leads, selectively switchable between resistive heating and capacitive moisture sensing.

Referring to FIG. 5, one or more microfluidic cells (501) may be formed in arrays having interposed electrical leads (502). The leads (502) may serve a variety of purposes including functioning as resistive heating elements to facilitate evaporation of the liquid-phase fluid. Alternatively, the electrical leads may also function as capacitive sensors to monitor levels of the liquid-phase fluid, thus controlling cyclical flooding and evaporation of said fluid, and optimizing concentration of the targeted analyte(s) within the liquid-phase fluid.

Figure 6:
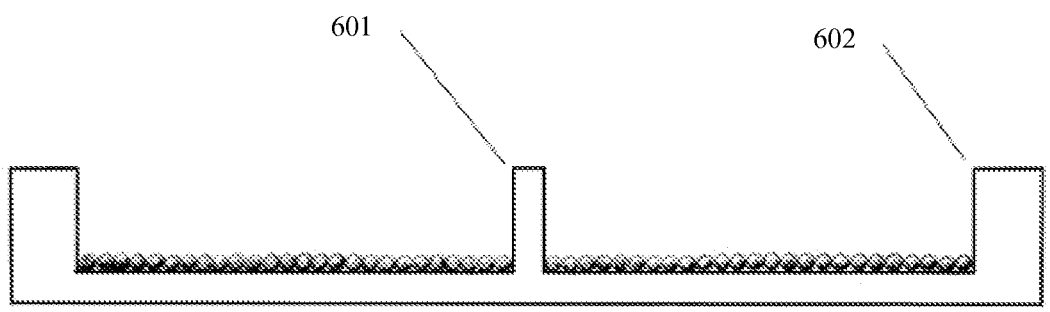
FIG. 6 illustrates one embodiment of the invention wherein the active regions feature a series of raised or embossed structures (e.g., pillars or spikes) to enhance nucleation of the analyte-bearing fluid, thus increasing transport of analytes into the medium.

Referring to FIG. 6, microfluidic cells (presented in cross-section) may employ structures and geometries to enhance nucleation of the condensing gas-phase fluid. Typical examples include pillars or spikes (601), and cells having sharply angled edges (602).

Figure 7:
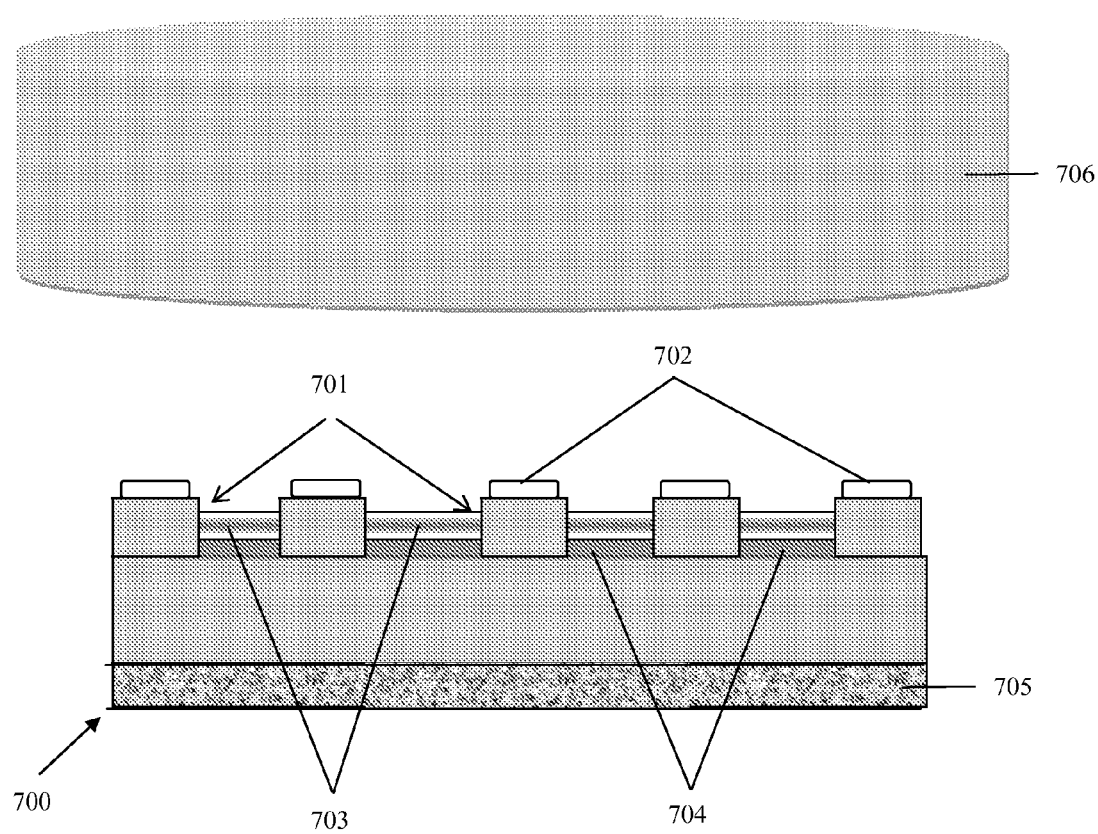
FIG. 7 illustrates one embodiment of active pumping of liquid/vapor exchange. In this embodiment a thermoelectric cooler cools the bulk substrate; resistive heating elements can be used to cyclically modulate the local temperature to drive evaporation. Liquid is condensed in the cells which interact with a SERS-active surface.

FIG. 7 illustrates one embodiment of the invention that includes active pumping of a liquid/vapor exchange. The thermal electric cooler maintains the temperature below the dew point of the ambient air. Resistive heating elements heat the air locally to drive evaporation of the liquid. When the heaters are turned off, the temperature drops below the dew point, and water vapor condenses on the condensation sites and fills up the reservoir. A confocal Raman probe can be used to provide excitation light and collect the scattered Raman light. 701 illustrates condensation sites of one embodiment of a device or system described herein. 702 illustrates resistive heating elements of one embodiment of a device or system described herein. 703 illustrates a condensed (liquid) medium of one embodiment of a device or system described herein. 704 illustrates a SERS active surface of one embodiment of a device or system described herein. 705 illustrates a thermoelectric cooler of one embodiment of a device or system described herein. 706 illustrates a confocal Raman probe of one embodiment of a device or system described herein.

Figure 8:
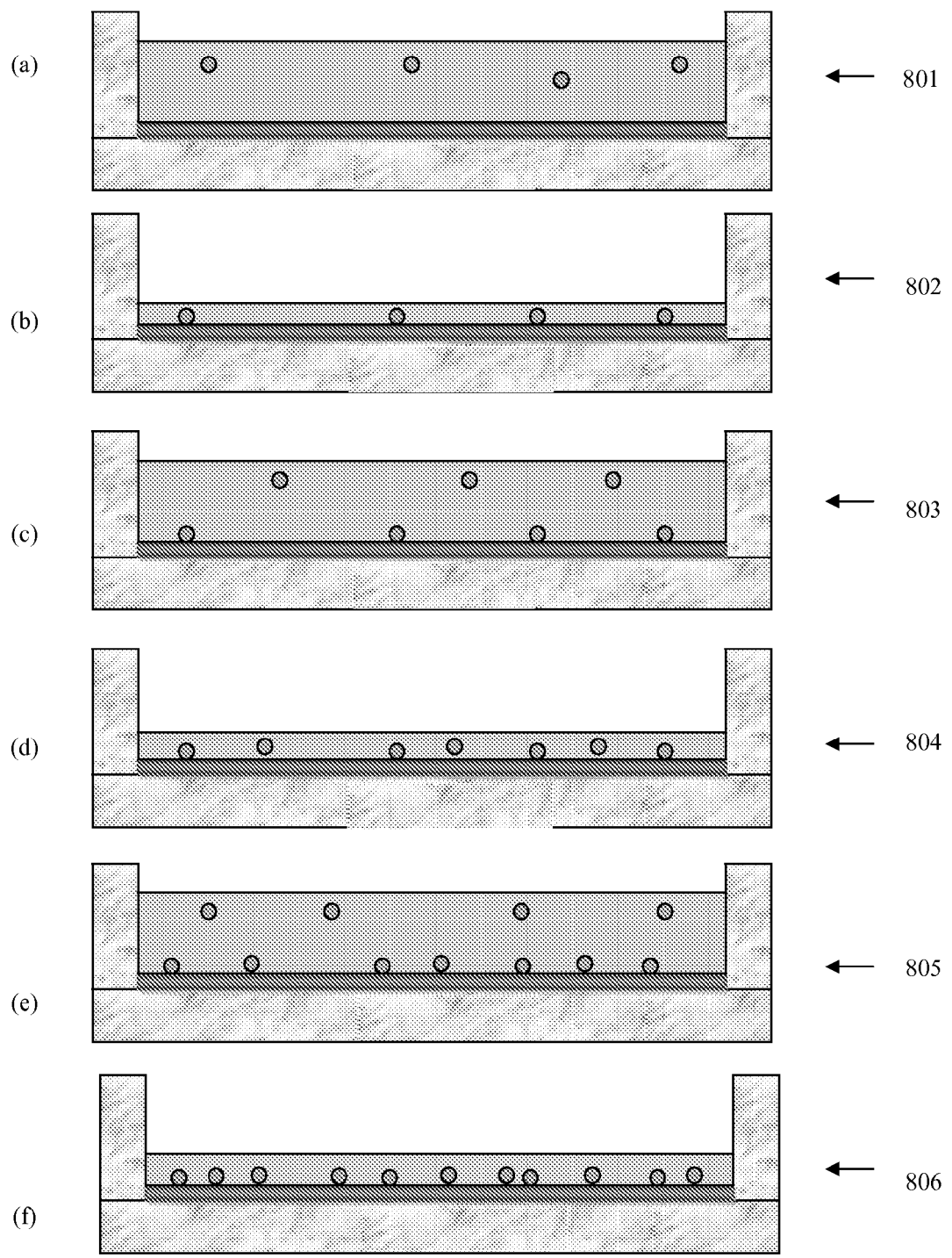
FIG. 8 illustrates that cyclical driving of the liquid vapor exchange modulates the liquid level and can provide consistent build up of analyte in the liquid.
Figure 9A:
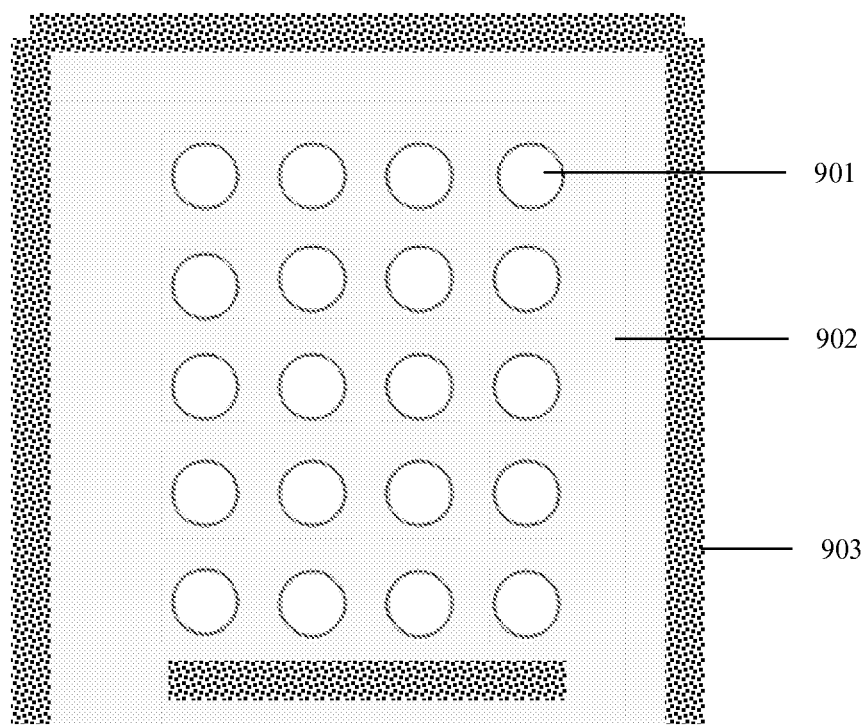
FIG. 9A is a top view showing an embodiment of an electrode structure in close proximity to cells for active driving of evaporation/condensation.
Figure 9B:
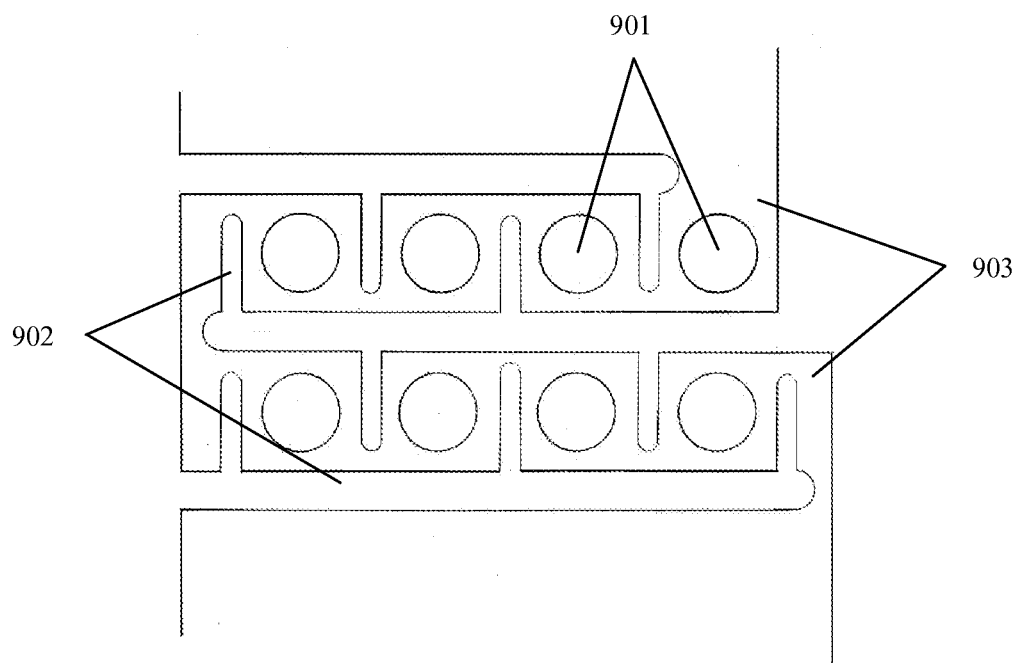
FIG. 9B shows one electrode with leads on the left and one electrode with leads on the right. Each individual electrode can be energized to function as a resistive heater. In addition, the electrodes can be used in combination to determine the capacitance between them. The capacitance measurement can be used to measure the relative depth of liquid water in the condensation cells.

FIG. 8 illustrates a preferable embodiment of the invention whereby active driving of the liquid/vapor exchange can provide gradual build up of an analyte within a liquid. For example, the illustrations describe a process through three such cycles (See 801-806). Repetitive cycling of the active vapor/liquid exchange allows for a buildup in concentration of analytes (dots). When vapor condenses into the condensation site, it enhances transport of airborne analytes into the liquid phase. When the liquid is evaporated, the analytes remain and adsorb to the SERS-active substrate. In some embodiments, repeating this process allows a large number of particles to collect in the fluid and adsorb onto the sensing region. It shall be understood that the number of cycles carried out can vary to accumulate analytes within the liquid phase of the chosen medium.

Preferable embodiments of the invention provide methods of filling (condensation) and un-filling (evaporation) reservoirs using apparatus described elsewhere herein.

Electrodes

The devices described herein may include one or more electrodes configured to perform a variety of functions. In some embodiments of the invention, electrodes are arranged on the top surface of a substrate described herein (e.g., in areas around and/or in contact with the cells, e.g., cells or microcells). In some embodiments, the one or more electrode or electrode array is arranged in a manner suitable for actively cycling the liquid/vapor exchange described herein. In preferable embodiments, the electrode serves as a resistive heating element utilized to facilitate the active cycling of the liquid/vapor exchange described herein. In more specific embodiments, the one or more electrode(s) is only utilized to serve as a resistive heating element utilized to facilitate the active cycling of the liquid/vapor exchange described herein. In other embodiments, the one or more electrode(s) are utilized for both resistive heating and capacitive sensing. In some embodiments provided herein, a device may comprise a first and a second electrode, wherein the first and/or second electrode(s) are utilized individually as resistive heating element(s). The first and second electrodes can also be used in combination to function as a capacitor, which can be utilized as a sensor. In certain embodiments, a microfluidic device may comprise a first electrode that functions as a heating element, and a second and third electrode that function together as a capacitive sensor. Alternative embodiments provide devices with a plurality of electrodes that function together only as a capacitive sensor (e.g., in embodiments wherein a non-heating mechanism of active cycling of the liquid/vapor exchange is utilized).

FIG. 9A illustrates an embodiment of the invention wherein the electrodes (902) are arranged on the top surface of the substrate (903). In certain instances an electrode of FIG. 9A shows a single resistive electrode. In specific embodiments, a "far west" and "far east" electrode form a current distribution bus providing a voltage drop over the electrical heater grid which produces heat. In some instances, the electrodes shown oriented in the north-south direction provide redundancy such that if any of the east-west-oriented electrodes fails, alternate current paths exist for heat to be produced near the failed electrode region.

FIG. 9B illustrates another embodiment, where two electrodes (902) are used, where individually each electrode functions as a resistive heating element. In certain instances, the electrodes can be used in combination, and function as a capacitor. In some instances, the capacitance between the (left & right) electrodes is a method for determining the depth of liquid water in the condensation cells (901). In various embodiments, the function of the electrodes can be switched between resistive heating mode and capacitive sensing modes.

Analyte Detection/SERS

The devices and processes provided in accordance with the invention can be suitable for or utilized for detecting any selected or targeted molecule. In some embodiments, a specific solvent (liquid) can be selected for a selected or targeted molecule. In one exemplary embodiment, a device or process described herein is utilized to detect TATP, DNT and/or TNT. In specific embodiments, a device or process described herein is utilized or suitable for detecting analytes (e.g., explosives) with low volatility, e.g., TNT or DNT. The saturated vapor concentrations at room temperature vary from ~10 ppb for TNT, ~$10^2$ ppb for DNT, to ~$10^6$ ppb for volatile species like TATP. Generally, techniques for detecting explosives require: (1) swabbing a sample, (2) heating the swab to ~400-450 K to vaporize the molecules, and then (3) using a variety of techniques MS, IMS, or Fido™, etc. for detecting and/or measuring an explosive.

With regard to selectivity, certain embodiments of the current invention allow measurement of various airborne molecules at room temperature without the need for swabbing. Table 1 describes the partitioning properties of DNT and toluene into water. As noted, the vapor pressure of toluene is six orders of magnitude higher than DNT. However, as illustrated in Table 1, DNT partitions into water at more than 5 orders of magnitude higher than toluene. The result is the equilibrium concentrations of the two molecules being comparable in magnitude: 50 mM (toluene) and 37 mM (DNT).

The saturation value of DNT in the gas-phase is 5e2 ppb, while in the liquid phase (e.g., water phase) it is 37 mM. To better understand the concentration aspects of the liquid medium, 5e2 ppb in the gas-phase at standard conditions corresponds to a volumetric concentration of 1.34e16 molecules per liter. In the liquid phase, 37 mM corresponds to a volumetric concentration of 2.23e22 molecules per liter. Condensing into the liquid phase provides approximately six orders of magnitude increase in volumetric concentration of analyte. Approximately three orders of magnitude are due to the partitioning of DNT into liquid phase, and three orders of magnitude are due to the liquid being a condensed medium.

TABLE 1

Comparison of partitioning properties of DNT and Toluene into water

| | Equilibrium Vapor pressure 300k (ppb) | Henry's Const (Atm $m^3$/mol) | Equilibrium aqueous concentration (mM) | Partitioning (relative to Toluene) |
|---|---|---|---|---|
| Toluene | 3e8 | 5e−3 | 50 | 1 |
| DNT | 5e2 | 1.35e−8 | 37 | 3.7e5 |

In certain instances, under equilibrium conditions six orders of magnitude of concentration can be achieved. However, in practical applications, it may be undesirable to wait for the long time periods required to reach equilibrium. Therefore, in certain embodiments of the present invention, high concentration can be achieved by actively pumping the liquid/vapor exchange. Active pumping can occur by cycling the temperature of the liquid region above and below the dew point. One method for doing this is to control the temperature of the bulk substrate to below the dew point, and then locally heat the condensation region using resistive elements (i.e. electrodes).

Moreover, in the preferred embodiments, SERS-active surfaces will be used to amplify Raman signals by six to ten orders of magnitude. This surface can consist of ~35 nm dia. (range is 5-100 nm) nanoparticles (Au or Ag), or thin ~5 nm layer of evaporated metal. These SERS-active surfaces could be protected or passivated by depositing a thin layer of material (e.g. SiO2) or a chemical monolayer (e.g. alkane-thiol). The hot surface can then be cleaned by NaOH or EtOH, etc. This will allow the surface to be cleaned and reused.

Condensation Sites & Cells

In some embodiments, a device described herein optionally comprises a condensation site (e.g., a cell, a microcell, a pillar, or the like). Therefore, in certain embodiments, though generally describing cells throughout this disclosure, it is optional to utilize other types of condensation sites than cells. For example, rather than cells described in various embodiments herein, a pillar or other condensation site may optionally be utilized.

In some embodiments, the device is a "flat substrate" device. In other embodiments, condensation sites can be cells (as discussed above). These cells could in principle be very large and very shallow, which could then be just a flat substrate. In other embodiments, microcells, as described above may also be utilized as condensation sites (e.g., at the sharp edges thereof).

In further or alternative embodiments, a device described herein comprises a pillar wetting surface. In various embodiments, the condensation cites can be pillars or grooved channels. In certain embodiments of the pillar configuration, the fluid may be contiguously connected.

Overall Sensor Chip (Hierarchy of Condensation Cells and Interrogation Regions)

Figure 12:
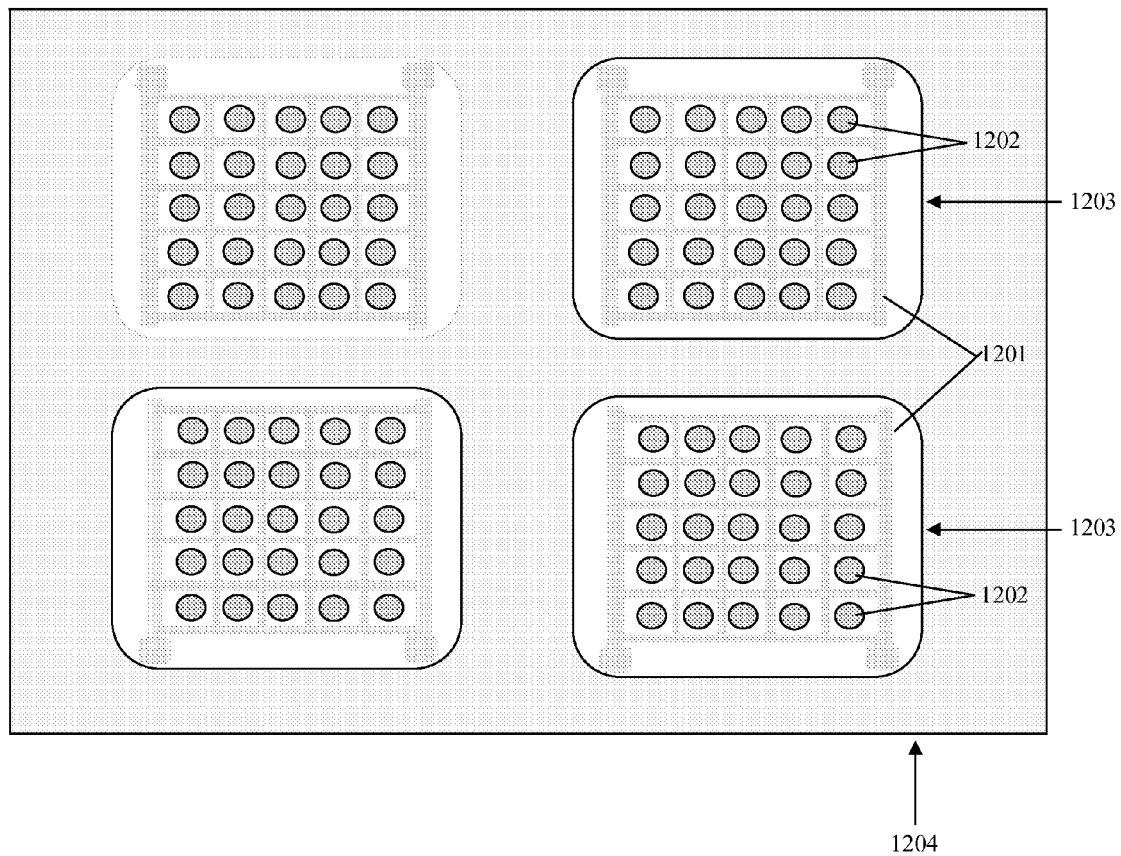
FIG. 12 illustrates one embodiment of the invention wherein the aforementioned active regions are deployed in a series of integrated arrays, interlinked by electrical leads to facilitate resistive heating, level sensing within the medium, and/or selective multiplexing of said active regions. Arrays may deploy multiple uniform active regions to enhance the accuracy of single-species analyte detection/analysis by redundancy, or multiple, non-uniform detection arrays capable of detecting/analyzing a multiplicity of analytes. The multiple integrated arrays can be formed on a single substrate or chip. The multiple integrated cell arrays can be formed on a single substrate or chip.

In one preferable embodiment of the invention, any of the device described herein (e.g., an overall sensor chip) can be designed in a hierarchical fashion. Such devices may comprise a plurality of ells, e.g., condensation cells or microcells. As discussed herein, each cell can be of any suitable size. In a specific embodiment, each condensation may be, e.g., 5 microns in diameter by 0.5 microns in deep. And in some embodiments, a single interrogation region (a region of the chip under test at a given time) has a characteristic size of 500 microns×500 microns. In such embodiments, an interrogation region consists of an array of condensation cells (e.g. 50×50 array of cells). FIG. 12 shows a plurality of integrated arrays of cells. 1204 illustrates a device comprises a plurality of arrays (1203), each comprising a plurality of cells (1202) with electrode(s) (1201).

In some embodiments, a device described herein may optionally comprise one or more interrogation regions, each interrogation region optionally function independently (e.g., be actively pumped individually and interrogated with a process for detection/measurement of an analyte, such as detecting/measuring with a Raman spectrometer, individually). Moreover, in some embodiments, each interrogation region is thermally isolated from other interrogation regions. In further or alternative embodiments, each interrogation region has separate electrode connections, and/or other independent configurations. A single chip can have many interrogation regions on the chip. In certain embodiments, any number of interrogation regions are optionally present on a "chip", on a single substrate, or in a device described herein, e.g., up to 100×100 array of interrogation regions or more are possible on an single chip. In preferred embodiments, smaller arrays are utilized however, e.g., 5×5 or 10×10 arrays (see FIG. 12 for an example).

Thermal Insulator Configuration

Figure 10:
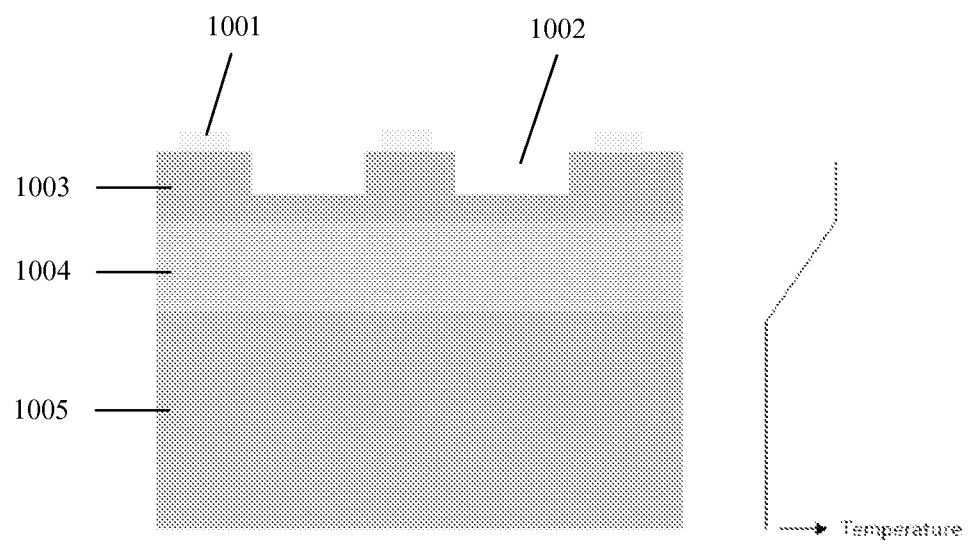
FIG. 10 illustrates a side view of one embodiment described herein, showing three primary layers: thermal backplane, thermal insulator, and detector substrate. The bulk of the substrate is the thermal backplane that is cooled from below by a TE cooler. It is separated from the detector substrate by a thin thermal insulator. This provides thermal isolation between the detector substrate on a short timescale (microseconds), while allowing heat transfer on a larger time scale (milliseconds).

In certain embodiments, any device described herein optionally comprises a thermal insulator region and a thermal backplate. In some embodiments, a thermal insulator region may be located between the detector substrate and the thermal backplane. In certain instances, this allows the heater to primarily heat only the small depth of the detector substrate/liquid, without heating the bulk of the substrate (i.e. thermal backplane). In some instances, this is advantageous because it can significantly decreases the power required to operate the active pump and increases the temporal response of the active pump. FIG. 10 illustrates a thermal insulator region (1004) between the detector substrate (1003) and the thermal backplane (1005), wherein 1001 is an electrode and 1002 is the detection region.

In some embodiments, electrodes described herein create a pulse of heat, by applying a short pulse of electrical current (of order of microseconds). In certain instances, this allows quick heating of the liquid causing it to be ejected, before the bulk of the substrate (thermal backplane) can be heated through thermal diffusion through the thermal insulator region. In some embodiments, the electrode is then turned off for a period of time (e.g., any suitable time, such as a significantly longer period of time than when turned on, e.g., about 10-1000 ms). In certain instances, this allows the colder temperature from the bulk substrate (i.e. thermal backplane) to diffuse through the thermal insulator into the detector substrate. In some embodiments, this cooling process allows water vapor in the air to condense onto the detector substrate. In some embodiments, this process can be repeated to cyclic drive evaporation/condensation, with minimal power requirements.

Therefore, in some embodiments, a device described herein comprises a substrate, the substrate comprising a thermal backplate, a thermal insulator, and a detector substrate. In specific embodiments, the detector substrate (nominally 0.5-1 microns thick) and thermal backplane (nominally 500 microns thick) may be comprised of any suitable material, e.g., silicon (thermal conductivity of k=130 W/m K) for efficient heat transfer. The thermal insulator (nominally 5 microns thick) can be comprised of any suitable material, e.g., glass (Silicon dioxide with thermal conductivity of k=1 W/m K). In certain instances, this insulator design significantly decreases the power required for operation, and increases the temporal response of the system.

Cell Configuration

In various embodiments, a device described herein comprises a substrate, with one or more cells (e.g., a cell, microcell, or the like) therein (e.g., etched therein). In specific embodiments, the cells or microcells have a diameter of about 10 nm to about 1000 microns, or about 10 nm to about 200 microns, and a depth of about 10 nm to about 1000 microns, or about 100 nm to about 500 nm. In some embodiments, the cells or microcells comprise a liquid component contained within one or more of the cell(s) or microcell(s) of a device described herein. Moreover, in certain embodiments, the cells or microcells comprise an active surface, the active surface used to facilitate detection and/or measurement of an analyte (e.g., a SERS-active surface/substrate). In specific embodiments, one or more cell or microcells of a device described herein comprises an active surface used to facilitate detection and/or measurement of an analyte (e.g., a SERS-active surface/substrate) confined therein.

Figure 11A:
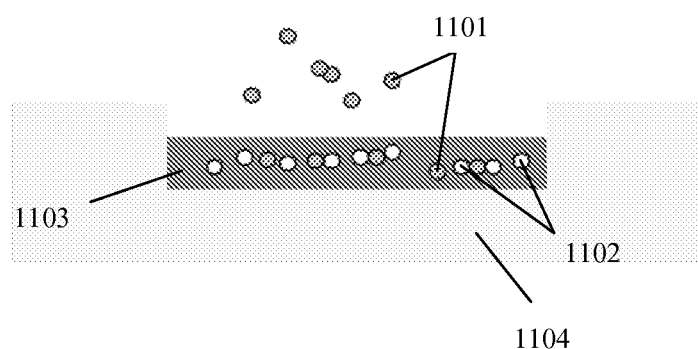
FIGS. 11A-11E illustrate various embodiments of SERS-active surfaces interacting with analyte, within the microfluidic cells. The SERS-active surfaces can be generated from one or assembly of nanoparticles, nanowires or nanorods, nano-textured substrates, or a combination of nanoparticles and nano-textured substrates.

FIG. 11A illustrates an embodiment of a cell or microcell described herein. Analytes transfer from gas phase into liquid phase. Then nanostructures (1102), such as metallic nanoparticles (e.g. Ag or Au), suspended in the liquid (1103) aggregate around analytes (1101), providing a SERS enhancement for detection of the analyte. 1104 illustrates a substrate for a device or system described herein.

Figure 11B:
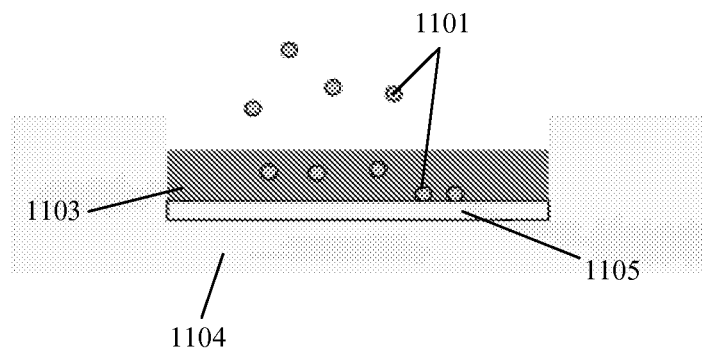

FIG. 11B illustrates another embodiment of a cell or microcell described herein. Analytes transfer from gas phase into liquid phase. Then analyte (1101) adsorbs onto metallized surface (1105) which provides SERS enhancement for detection of the analyte. The metallized surface can be nanostructured (e.g. by electrochemical roughening) in order to increase the SERS enhancement effect, providing facile detection of the analyte.

Figure 11C:
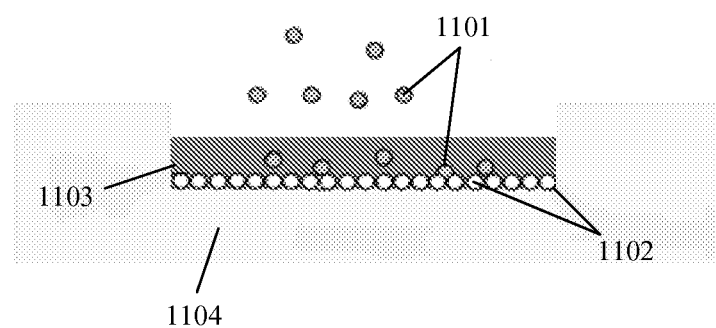

FIG. 11C illustrates another embodiment of a cell or microcell described herein. Analytes transfer from gas phase into liquid phase (1103). Nanostructures (1102), such as metallic nanoparticles (e.g. Au or Ag), attached to the substrate (e.g. using well-known silane chemistry) (1104) provide a nanostructured and metallized surface to which analytes (1101) adsorb. The nanoparticles provide SERS enhancement of the analytes, providing facile detection of the analyte.

Figure 11D:
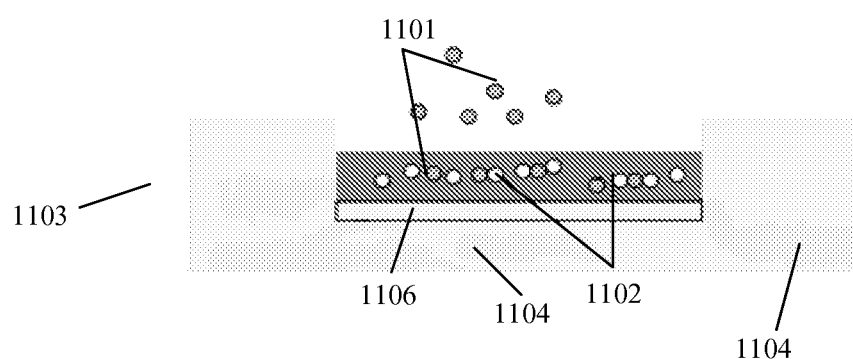
Figure 11E:
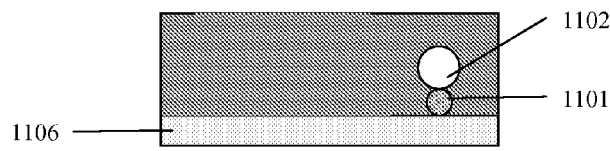

FIG. 11D illustrates another embodiment of a cell or microcell described herein. A combination of nanoparticles (1102) and surface-bound nanoparticles and/or macroscopically smooth metallic substrates (1106) to provide sandwich-type junction geometry for SERS enhancement of the analytes, providing facile detection of the analyte. The analyte can be sandwiched between the nanoparticle (1102) in solution and the surface-bound nanoparticle (1106) or between the nanoparticle in solution and the macroscopically smooth metallic substrate (1106), creating SERS-active hot spots in the form of metal/molecule/metal junction structure. (see FIG. 11E).

In certain embodiments, the cells further comprise an aggregation inducing compound. In certain instances, the addition of 'aggregation inducing' compounds into embodiments bearing suspended nanoparticles forces aggregation events due to a collapse of the Coulombic repulsion existing in a colloidal nanoparticle suspensions. Aggregation may be induced by the introduction of charged species such as sodium chloride or other salts which disrupts the surface charge balance enveloping suspended nanoparticles. Alternatively, 'nanoparticle linker molecules' such as 1,2-diaminoethane, 1,4-diaminobutane or 1,3,5-triaminopentane may be used in embodiments wherein suspended nanoparticles are present. In certain instances, these nanoparticle linker molecules can act to form physical linkages between nanoparticles. Since some analyte moieties may not cause nanoparticle aggregation to occur at a given set of conditions (for instance the analyte concentration may be very low or the analyte does not natively induce a nanoparticle collapse event), 'aggregation inducing' molecules or molecules thereby reduce the detection limit for these analyte moieties. Such 'aggregation inducing' molecules or compounds may be added to analyte gas mixtures to cause nanoparticle aggregation upon contact with and transfer into the liquid detection phase. Alternatively, 'aggregation inducing' molecules or compounds may be added directly to the cell, e.g., during the detection phase by direct injection.

Alternate Embodiments

In some embodiments, devices and processes of the present invention do not require the active cycling of the liquid/vapor exchange. For example, in some embodiments, a liquid droplet (e.g. 0.1 microliter) comprising an active surface component (e.g., nanoparticles suspended or otherwise contained therein) is introduced into a microcell or onto a surface, without active cyclic pumping (i.e., an "inactive pump" or a "passive case"). While this method may not have the temporal response for absorbing gas-phase analyte as the active pumping, it may be advantageous in certain instances. For example, it may be simpler to implement and perform sufficiently.

In certain embodiments, the local humidity can be controlled, in any suitable manner, to stabilize the liquid droplet. For example, additional water droplets may be located in close proximity to a central nanoparticle-containing liquid droplet. (This can be done to increase local humidity, but is optional). Separately, humidified or de-humidified gas, for instance created by bubbling $N_2$ gas through the water, may be added to control local humidity.

The local temperature can also be controlled to stabilize the liquid droplet. For example, a PID control system can be used to monitor local humidity and temperature to maintain the temperature of the liquid droplet at the dew point ($T_{dew}$). When the temperature is held at $T_{dew}$, the flux of water molecules condensing into the droplet equals the flux of water molecules evaporating from the liquid surface.

Gas-phase molecules can be transferred to the nanoparticle droplet using at least two methods: (1) When the temperature is held at $T_{dew}$, gas-phase analyte molecules are delivered to the liquid droplet by first adsorbing to the gas-phase water molecules which then condense on the surface of the liquid droplet. (2) Gas-phase analyte may also adsorb directly onto the surface of the liquid droplet due to condensation effects unrelated to humidity condensation.

Once the gas-phase analyte is absorbed into the nanoparticle-containing water droplet, the analyte can be measured using SERS. One advantage of the Inactive Pumping over Active Pumping is that the water droplet can contain suspended colloidal nanoparticles that can aggregate in the presence of analyte. In the active pumping case, the water is cyclically evaporated so one cannot maintain a solution of nanoparticles, and all the SERS-active particles are then deposited on the substrate surface (and not in suspension).

Regarding certain specific embodiments for the active surface components (e.g., SERS-active surfaces) of the "Inactive Pump" (i.e. passive case), nanoparticles can be placed in colloid form within the liquid droplet. These nanoparticles can then aggregate around absorbed analyte molecules, causing a local electromagnetic field enhancement, which produces SERS spectra when stimulated by a laser of the appropriate wavelength. In certain embodiments, a combination of nanoparticles and SERS-active substrates are provided in the fluid to create the SERS effect. Several cases are presented that illustrate these combinations. In certain embodiments, a SERS-active substrate can itself consist of immobilized nanoparticles, or a thin (~5 nm) metallic film. In certain embodiments, the nanoparticles can be Au or Ag and range in size from 10 nm to 200 nm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:
1. A microfluidic system for the detection of airborne analytes, the system comprising:

at least one condensation site comprising a microcell with a bottom surface, enclosed sidewalls, and top surface partially open to air;

a fluid medium contained in the microcell, the fluid medium comprising an air/liquid interface providing selectivity for targeted airborne analytes;

nanostructures having surface-enhanced-Raman-spectroscopy (SERS) active surfaces for the adsorption of analytes, the nanostructures adhered to the bottom surface of the microcell;

a cyclical vapor/liquid exchange pumping system that cycles the fluid medium through evaporation and condensation phases, whereby analytes condense with the fluid medium and aggregate with the nanostructures; and, a Raman spectrometer, wherein cycling the fluid medium through evaporation and condensation phases comprises active cycling of the fluid medium through the evaporation phase, the condensation phase, or both.

2. The system of claim 1, the microcells having a horizontal dimension of about 0.01 microns to about 1000 microns, and a depth of about 0.01 microns to about 1000 microns.

3. The system of claim 1, the nanostructures comprising a plurality of gold nanospheres having diameters of about 15 nm to about 100 nm.

4. The system of claim 1 wherein active cycling of the fluid medium through the evaporation phase comprises reducing pressure on the fluid medium, heating the fluid medium, or a combination thereof.

5. The system of claim 1 wherein active cycling of the fluid medium through the condensation phase comprises increasing pressure on the fluid medium, cooling the fluid medium, or a combination thereof.

6. A process for detecting airborne analytes, the process comprising:

confining a fluid medium in a microcell having a bottom surface, enclosed sidewalls, and top surface partially open to air;

wherein, the fluid medium comprises an air/liquid interface providing selectivity for a targeted airborne analyte, and nanostructures adhered to the bottom surface of the microcell have surface-enhanced-Raman-spectroscopy (SERS) active surfaces for the adsorption of analytes;

contacting an air sample with the air/liquid interface of the fluid medium;

cycling the fluid medium through evaporation and condensation phases, whereby analytes condense with the fluid medium and aggregate with the nanostructures;

interrogating the microcell with a Raman spectrometer; and, determining an amount of analyte present in the air sample based on a surface-enhanced-Raman-spectroscopy (SERS) spectrum obtained with the spectrometer, wherein cycling of the fluid medium through evaporation and condensation phases comprises active cycling of the fluid medium through the evaporation phase, the condensation phase, or both.

7. The process of claim 6, the microcell having a horizontal dimension of about 0.01 microns to about 1000 microns, and a depth of about 0.01 microns to about 1000 microns.

8. The process of claim 6, the nanostructures comprising a plurality of gold nanospheres having diameters of about 15 nm to about 100 nm.

9. The process of claim 6 wherein active cycling of the fluid medium through the evaporation phase comprises reducing pressure on the fluid medium, heating the fluid medium, or a combination thereof.

10. The process of claim 6 wherein active cycling of the fluid medium through the condensation phase comprises increasing pressure on the fluid medium, cooling the fluid medium, or a combination thereof.

* * * * *